United States Patent
Bhagwandin

(10) Patent No.: US 10,507,208 B2
(45) Date of Patent: *Dec. 17, 2019

(54) COMPOSITIONS, PACKAGED PHARMACEUTICALS, AND METHODS OF USING HEDGEHOG PATHWAY MODULATORS FOR THE SENSITIZATION OF RESISTANT TUMORS

(71) Applicant: Vikash J. Bhagwandin, San Mateo, CA (US)

(72) Inventor: Vikash J. Bhagwandin, San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/291,915

(22) Filed: Oct. 12, 2016

(65) Prior Publication Data

US 2017/0100393 A1    Apr. 13, 2017

Related U.S. Application Data

(60) Provisional application No. 62/240,500, filed on Oct. 12, 2015, provisional application No. 62/240,504, filed on Oct. 12, 2015, provisional application No. 62/240,507, filed on Oct. 12, 2015, provisional application No. 62/240,510, filed on Oct. 12, 2015, provisional application No. 62/240,513, filed on Oct. 12, 2015.

(51) Int. Cl.

| | |
|---|---|
| *A61K 31/497* | (2006.01) |
| *A61K 31/496* | (2006.01) |
| *A61K 45/06* | (2006.01) |
| *A61K 31/337* | (2006.01) |
| *A61K 31/475* | (2006.01) |
| *A61K 31/593* | (2006.01) |
| *A61K 33/36* | (2006.01) |
| *A61K 31/335* | (2006.01) |
| *A61K 31/405* | (2006.01) |

(52) U.S. Cl.
CPC .......... *A61K 31/496* (2013.01); *A61K 31/337* (2013.01); *A61K 31/475* (2013.01); *A61K 31/593* (2013.01); *A61K 33/36* (2013.01); *A61K 45/06* (2013.01)

(58) Field of Classification Search
None
See application file for complete search history.

(56) References Cited

U.S. PATENT DOCUMENTS

| | | |
|---|---|---|
| 2007/0281040 A1 | 12/2007 | Weichselbaum et al. |
| 2014/0315920 A1 | 10/2014 | Virca et al. |

FOREIGN PATENT DOCUMENTS

| | | |
|---|---|---|
| WO | 2004105696 A2 | 12/2004 |
| WO | 2005000208 A2 | 1/2005 |
| WO | 2008089185 A2 | 7/2008 |

OTHER PUBLICATIONS

Hardin et al. (1988) Antimicrob. Agents Chemother. 32:1310-1313.
Gupta et al. (1991) J. Clin. Invest. 87(4):1467-1469.
Gottesman et al. (1993) Annu. Rev. Biochem. 62:385-427.
Vreugdenhil et al. (1993) Ann. Hematol. 67(3):107-109.
Kurosawa et al. (1996) Ann. Hematol. 72(1):17-21.
Miyama et al. (1998) Antimicrob. Agents Chemother. 42:1738-1744.
Rocchi et al. (2000) Biochem. Biophys. Res. Commun. 271:42-46.
Shepard et al. (2003) Int. J. Cancer 103:121-125.
Houghton et al. (2004) Cancer Res. 64:2333-2337.
Ozvegy-Laczka et al. (2004) Mol. Pharmacol. 65:1485-1495.
Burger et al. (2005) Cancer Biol. Ther. 4(7)747-752.
Takada et al. (2005) Drug Metab. Dispos. 33:905-909.
Nakanishi et al. (2006) Blood 108:678-684.
Lou et al. (2007) Oncogene 26:1357-1360.
Sims-Mourtada et al (2007) Oncogene 26:5674-5679.
Zhang et al. (2009) Neoplasia 11:96-101.
Kim et al. (2010) Cancer Cell. 17:388-399.
Singh et al. (2011) Oncogene 30:4874-4886.
Tapaninen et al. (2011) J. Clin. Pharmacol. 51:359-367.
Kim et al. (2013) Cancer Cell. 23:23-34.
Rudin et al. (2013) J. Thorac. Oncol. 8(5):619-623.
Chen et al. (2014) Molecular Carcinogenesis 53:625-634.
Tsubamoto et al. (2014) Anticancer. Res. 34(5):2481-2488.
Tsubamoto et al. (2014) Anticancer. Res. 34(7):3839-3844.
Tsubamoto et al. (2015) Anticancer. Res. 35(7):4191-4196.
Tsubamoto et al. (2015) Anticancer. Res. 35(9):4923-4928.
Xu et al. (2010) Proc. Natl. Acad. Sci. USA 107:4764-4769.
Aftab et al. (2011) Cancer Res. 71:6764-6772.
Nacev et al. (2011) J. Biol. Chem. 286:44045-44056.
Liu et al. (2014) Autophagy 10:1241-1255.
Vincristine Product Insert.
Docetaxel Product Insert.

*Primary Examiner* — Shobha Kantamneni

(57) ABSTRACT

Compositions, packaged pharmaceuticals, and methods of treatment by the sensitization of resistant tumors are provided. The compositions comprise a combination of a hedgehog pathway modulator, such as itraconazole, and a chemotherapeutic agent. Tumor cells in mammalian subjects treated with the hedgehog pathway modulator are sensitized to the effects of the chemotherapeutic agent, thus increasing the therapeutic index of the agent and reducing toxicity to the subject.

8 Claims, 14 Drawing Sheets

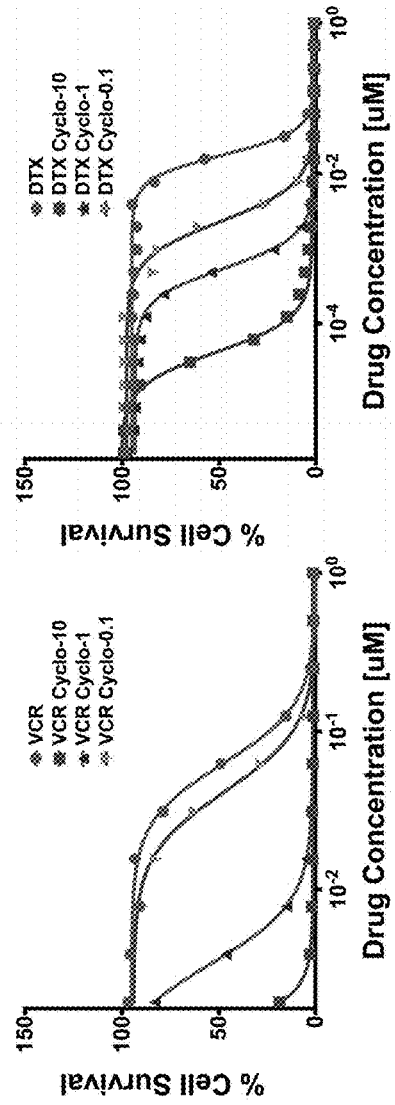
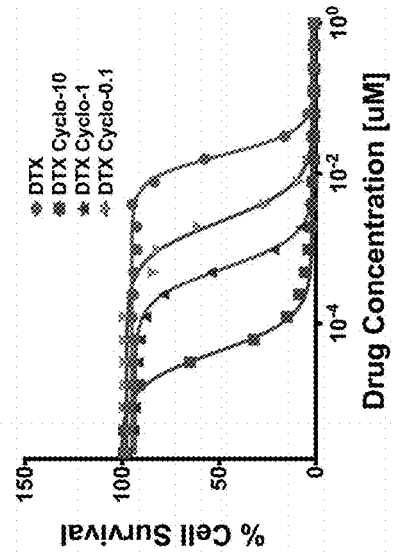
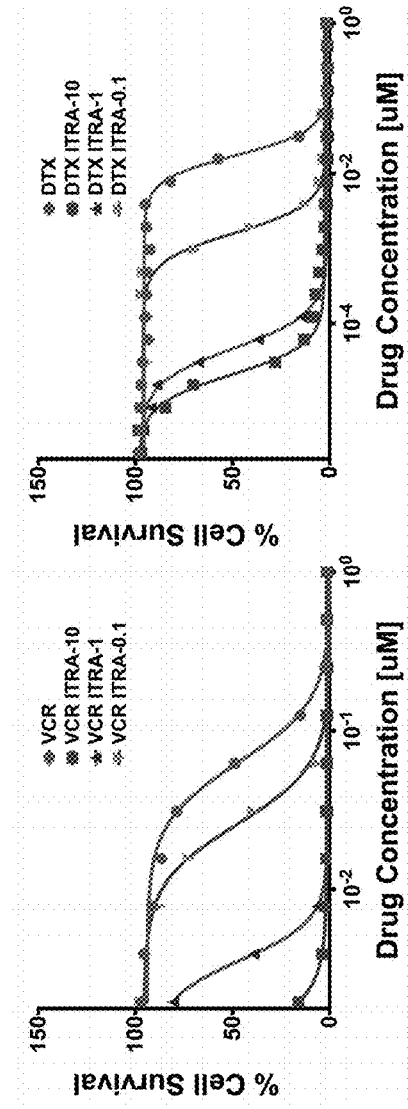
FIG. 10A, FIG. 10B, FIG. 10C, FIG. 10D — H295 Cell Line

Kelly Cell Line
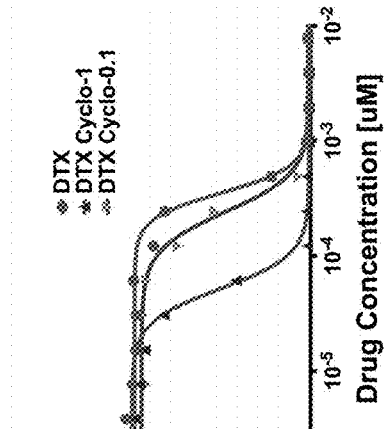
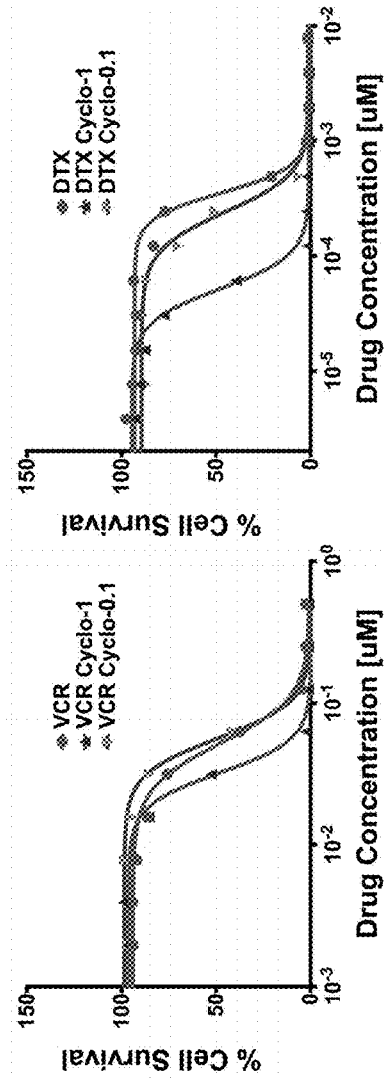
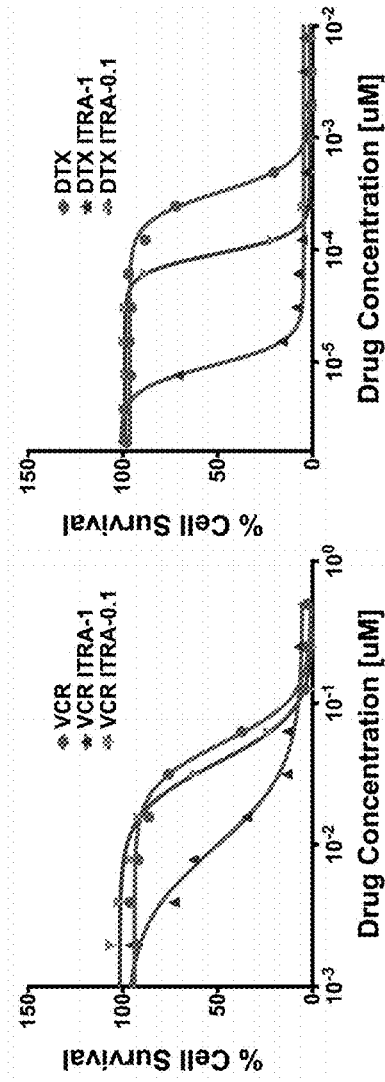

Caco-2 Cell Line

HeLa Cell Line

COMPOSITIONS, PACKAGED PHARMACEUTICALS, AND METHODS OF USING HEDGEHOG PATHWAY MODULATORS FOR THE SENSITIZATION OF RESISTANT TUMORS

CROSS-REFERENCE TO RELATED APPLICATIONS

This application claims the benefit of U.S. Provisional Application Nos. 62/240,500; 62/240,504; 62/240,507; 62/240,510; and 62/240,513; all filed on Oct. 12, 2015, the disclosures each of which are incorporated herein by reference in their entireties.

BACKGROUND OF THE INVENTION

Most first-line chemotherapy drugs can destroy bulk tumor cells but fail to eliminate cancer stem cells, the cells that contribute to recurrence or relapse of the tumor, further progression, metastasis, and subsequent chemoresistance. This indicates that cancer stem cells may be "intrinsically" resistant to chemotherapy or that resistance is induced during first-line of therapy via acquisition of mutations, which are carried into and exist during the second-line of therapy settings. Therefore, the targeting of cancer stem cells as a first-line of therapy setting may eliminate intrinsically resistant cancer cells, prevent acquisition of resistance mutations, limit further progression and metastasis of cancer, and may also be applicable in the second-line therapy setting where responsive cancer cells can exist. Cancer cells, and more specifically cancer stem cells, can express one or multiple ATP Binding Cassette (ABC) transporters as a mechanism of resistance to chemotherapy drugs. ABC transporter proteins can facilitate the efflux of drugs from cancer cells rendering them resistant. The efflux of drugs from cancer cells means that higher concentrations of drug are required to achieve cell death, and at those concentrations the drug can be toxic to patients, essentially reducing the therapeutic index of the drug. Many known inhibitors of ABC transporters such as verapamil, reserpine, and cyclosporine, when used sequentially or in combination with other drugs, directly reduce or prevent the removal of the chemotherapeutic drug from the cell, making the drug more effective at lower concentrations. By increasing the intracellular concentration of the drug, and reducing initial treatment concentrations necessary to achieve cancer cell death the therapeutic window of the drug is improved and toxicity to the patient is alleviated. However, the concentration of ABC transport inhibitor necessary to turn off the transporters is too toxic to be used in patients, and the inhibitors are therefore not effective for use in combination therapy. Gottesman et al. (1993) *Annu. Rev. Biochem.* 62:385-427.

In some instances, ABC transporter activity is tightly regulated by sequestration of the transporter to intracellular compartments. Rocchi et al. (2000) *Biochem. Biophys. Res. Commun.* 271:42-6. For example, the translocation of ABC transporter, ABCG2, to the cell membrane is dependent on post-translational modification through phosphorylation by Akt kinase. Takada et al. (2005) *Drug Metab. Dispos.* 33:905-9. In cells expressing ABCG2, Akt inhibitors such as, Gleevec, LY294002, or LY335979, have been shown to reduce or completely eliminate translocation of transporter to the cell membrane and either reduce or completely abrogate transporter activity, thereby sensitizing resistant cells to drugs. Shepard et al. (2003) *Int. J. Cancer* 103:121-5; Nakanishi et al. (2006) *Blood* 108:678-84; Burger et al. (2005) *Cancer Biol. Ther.* 4:747-52; Ozvegy-Laczka et al. (2004) *Mol. Pharmacol.* 65:1485-95; Houghton et al. (2004) *Cancer Res.* 64:2333-7. However, it has been shown that this therapeutic strategy leads to compensatory elevations in transporter expression to maintain resistance, and is therefore insufficient for efficacious therapeutic applications.

Another strategy for overcoming ABC transporter-related drug resistance is to inhibit pathways that control ABC transporter expression in the resistant cancer cells, including cancer stem cells. The combination of Smo (smoothened) antagonist, cyclopamine, with chemotherapy drugs has been shown to reduce ABCG2 and ABCB1/MDR1 activity and to increase cancer cell death as compared to drug alone in vitro, by mechanisms that have yet to be identified. Singh et al. (2011) *Oncogene* 30:4874-86; Zhang et al. (2009) *Neoplasia* 11:96-101; Sims-Mourtada et al. (2007) *Oncogene* 26:5674-9; Lou et al. (2007) *Oncogene* 26:1357-60. However, cyclopamine is a toxic alkaloid that is lethal to humans with no feasible therapeutic application.

Itraconazole is a prescription-only antifungal agent that has been used to treat fungal infections such as, nail fungus, *Aspergillosis, Candidiasis, Cryptococcosis*, and *Histoplasmosis*. Hardin et al. (1988) *Antimicrob. Agents Chemother.* 32:1310-3. Itraconazole has also been shown to inhibit P-gp/MDR-1/ABCB1 activity directly. Miyama et al. (1998) *Antimicrob. Agents Chemother.* 42:1738-44. It has also been shown to be a strong CYP3A4, cytochrome P450 3A4 inhibitor. Tapaninen et al. (2011) *J. Clin. Pharmacol.* 51:359-67. Recently, itraconazole, arsenic trioxide, vitamin D3, and various other agents have been shown to inhibit the hedgehog pathway. Kim et al. (2010) *Cancer Cell.* 17:388-99. It was shown that these compounds could be used as single agents to inhibit growth or induce cell death of tumors containing a deregulated hedgehog pathway or mutations in Ptc, Smo or Gli proteins. Kim et al. (2013) *Cancer Cell.* 23:23-34. Itraconazole is currently in clinical trials for the treatment of several tumor types that are driven by the deregulation of the hedgehog pathway. Itraconazole has been shown to inhibit ABCG2 and ABCB1/MDR1 in cells that were artificially engineered to replicate acquired chemoresistance or in cells from heavily pretreated patients or patients treated as second-line of therapy in vitro. However, these experiments were performed using cytotoxic and non-therapeutic dosages in combination with dye substrates as a readout. Gupta et al. (1991) *J. Clin. Invest.* 87(4):1467-1469; Kurosawa et al. (1996) *Ann. Hematol.* 72(1):17-21. In the above context, acquired chemoresistance may be defined by when cancer cells are exposed to chemotherapeutic drugs until the cell "acquires" mutations that activate mechanisms and render the cancer cells resistant to chemotherapies.

Itraconazole has also been shown to increase survival of patients when administered in combination with second-line therapy for AML (acute myelogenous leukemia), ALL (acute lymphoblastic leukemia); Vreugdenhil et al. (1993) *Ann. Hematol.* 67(3):107-109, pancreatic cancer; Tsubamoto et al. (2015) *Anticancer. Res.* 35(7):4191-4196, biliary tract cancer; Tsubamoto et al. (2015) *Anticancer. Res.* 35(9):4923-4927, triple-negative breast cancer; Tsubamoto et al. (2014) *Anticancer. Res.* 34(7):3839-3844, ovarian cancer; Tsubamoto et al. (2014) *Anticancer. Res.* 34(5):2481-2487, and non-squamous NSCLC (non-small cell lung carcinoma) Rudin et al. (2013) *J. Thorac. Oncol.* 8(5):619-623. However, in these contexts itraconazole was administered to heavily pretreated patients in the second-line of therapy settings. Those patients may have acquired mutations conferring resistance to the chemotherapies due to their prior treatment with the chemotherapeutic agents.

There is thus a need for improved compounds, compositions, packaged pharmaceuticals, and methods for overcoming chemoresistance in tumor cells, particularly in tumor cells expressing ABC transporters, as first-line of therapy.

SUMMARY OF THE INVENTION

The present invention addresses these and other problems by providing in various aspects compositions, packaged pharmaceuticals, and methods for modulating the hedgehog pathway in order to reduce or eliminate MYC expression or modulate the activity of other regulators that can lead to the down-regulation of ABC transporter expression and that alleviate chemoresistance in cancer cells. The modulation of the hedgehog pathway is used in combination with chemotherapy drugs to increase the therapeutic index in patients for several cancer types and to reduce related side effects of these drugs. The compositions, packaged pharmaceuticals, and methods may include any chemotherapy drug class, formulation, dosage, or therapeutic schedule determined by pre-clinical and clinical trials for each cancer type as a first-line of therapy or for responsive cells in the second-line of therapy.

In specific embodiments, the invention relates to the repurposing of a hedgehog pathway modulator, including itraconazole, arsenic trioxide, vitamin D3, and various other agent, to reduce or eliminate ABC transporter expression, and therefore to reduce or eliminate ABC transporter activity in resistant cancer cells and thus to increase the therapeutic index of chemotherapy drugs.

In other aspects, the invention provides for the repurposing of experimental and FDA approved therapeutic compounds that are intended for the inhibition of molecules or pathways unrelated to the hedgehog pathway, but that can have inhibitory effects on the hedgehog pathway for the inactivation of ABC transporters. These compounds are less toxic and more tolerable to patients when used in combination with drugs that improve the therapeutic index of the drug and reduce the related side effects of the drug as compared to when the drug is used alone.

BRIEF DESCRIPTION OF THE DRAWINGS

FIGS. 10A-10L. A set of pre-clinical data demonstrating a preferred embodiment of the invention demonstrating a "dose de-escalation" strategy with the use of cyclopamine (a positive control and toxic antagonist of the hedgehog pathway), and itraconazole combined with vinca alkaloid; vincristine, and taxane; docetaxel in H295 (adrenal cortical carcinoma), Kelly (neuroblastoma (childhood brain cancer)), HeLa (cervical cancer) and Caco-2 (colon or colorectal cancer) cell lines.

DETAILED DESCRIPTION OF THE INVENTION

The present invention relates in general to the field of cancer therapy. In particular, the invention relates to the sensitization of chemoresistant cancer cells using modulators of the hedgehog pathway. Specifically, the invention relates to the sensitization of chemoresistant cancer cells through the reduction, elimination and/or inactivation of pumps responsible for the removal of chemotherapy drugs from cancer cells. More particularly, the invention relates to the modulation of signaling pathways that regulate pump expression in cancer cells. Specifically, the present invention relates to the modulation of any component of the hedgehog pathway that can result in the down-regulation of MYC an activator or other regulators of ABC transporters, and can render chemoresistant cancer cells vulnerable to chemotherapy drugs. The invention is also further applicable to the repurposing of experimental and FDA approved compounds that can modulate the hedgehog pathway and can lead to the sensitization of chemoresistant cancer cells to chemotherapy drugs.

The present disclosure provides methods of achieving enhanced synergistic killing of chemoresistant cancer cells when compounds are combined, one is a modulator of the hedgehog pathway, and the second is a chemotherapy drug that is a known substrate of ABC transporters. The combination makes the cells vulnerable to chemotherapy drugs at lower concentrations while reducing the toxicity to the patient.

The following embodiments of the invention describe several methods of combining hedgehog pathway modulators with chemotherapy drug to achieve an improved therapeutic index in patients. The compositions and methods may include any chemotherapy drug class, formulation, dosage and therapeutic schedule determined by pre-clinical and clinical trials for each cancer type as a first-line of therapy or for responsive cells in the second-line of therapy.

Figure 1:
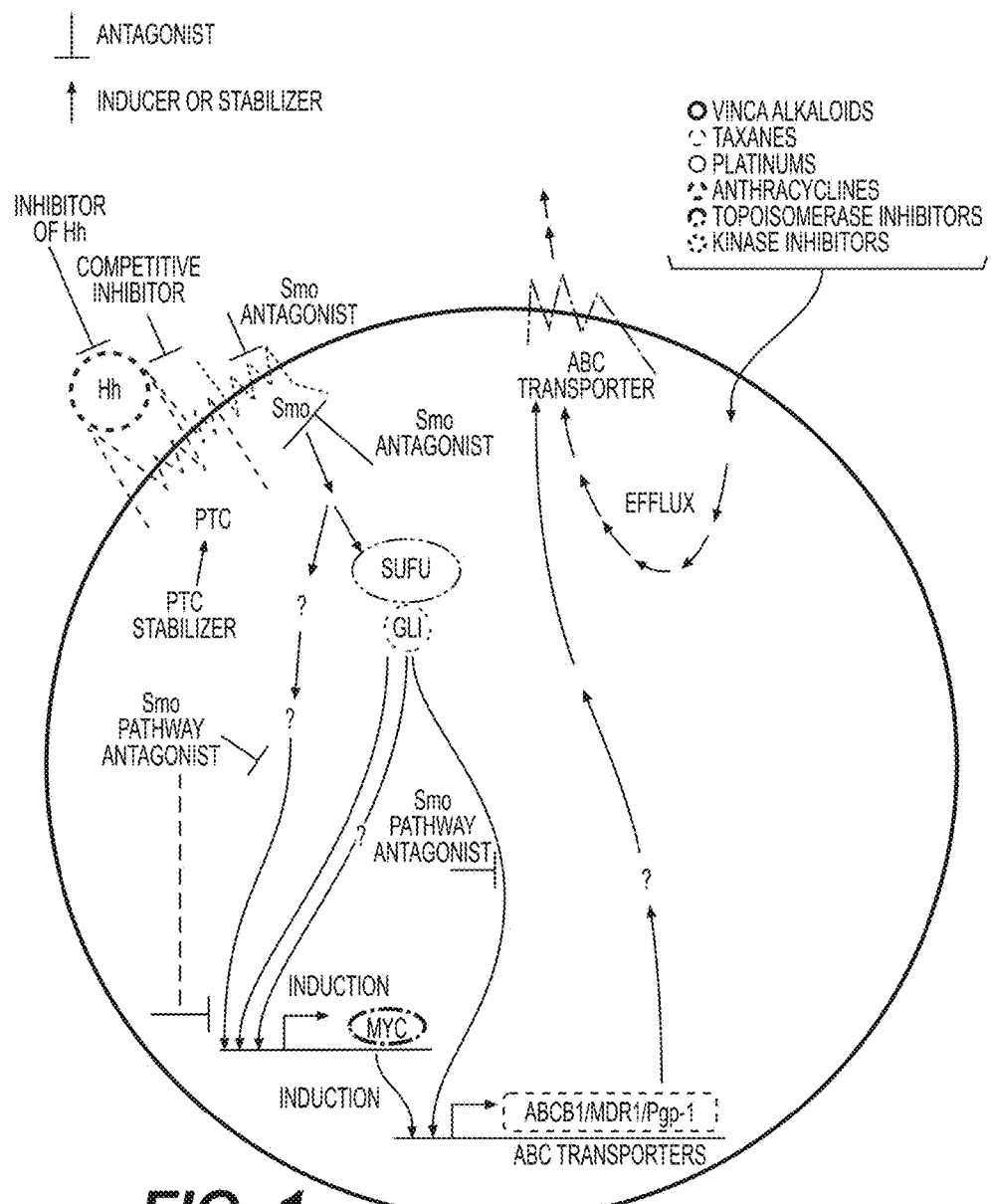
FIG. 1. A diagram of the hedgehog pathway regulation of ABC transporters, which depicts exemplary points of inhibition where the invention can be applied to reduce ABC transporter expression.

The hedgehog pathway contains several points of regulation that can be exploited as targets for the downregulation of ABC transporters, outlined in FIG. 1. Compounds or biologics are used to modulate the hedgehog pathway at any of the regulatory points indicated in FIG. 1, which results in the downregulation of MYC or other regulators of ABC transporters. When MYC or other regulators are downregulated the ABC transporters are downregulated. The downregulation of ABC transporters renders the cell sensitive to lower concentrations of chemotherapy drugs.

Figure 2:
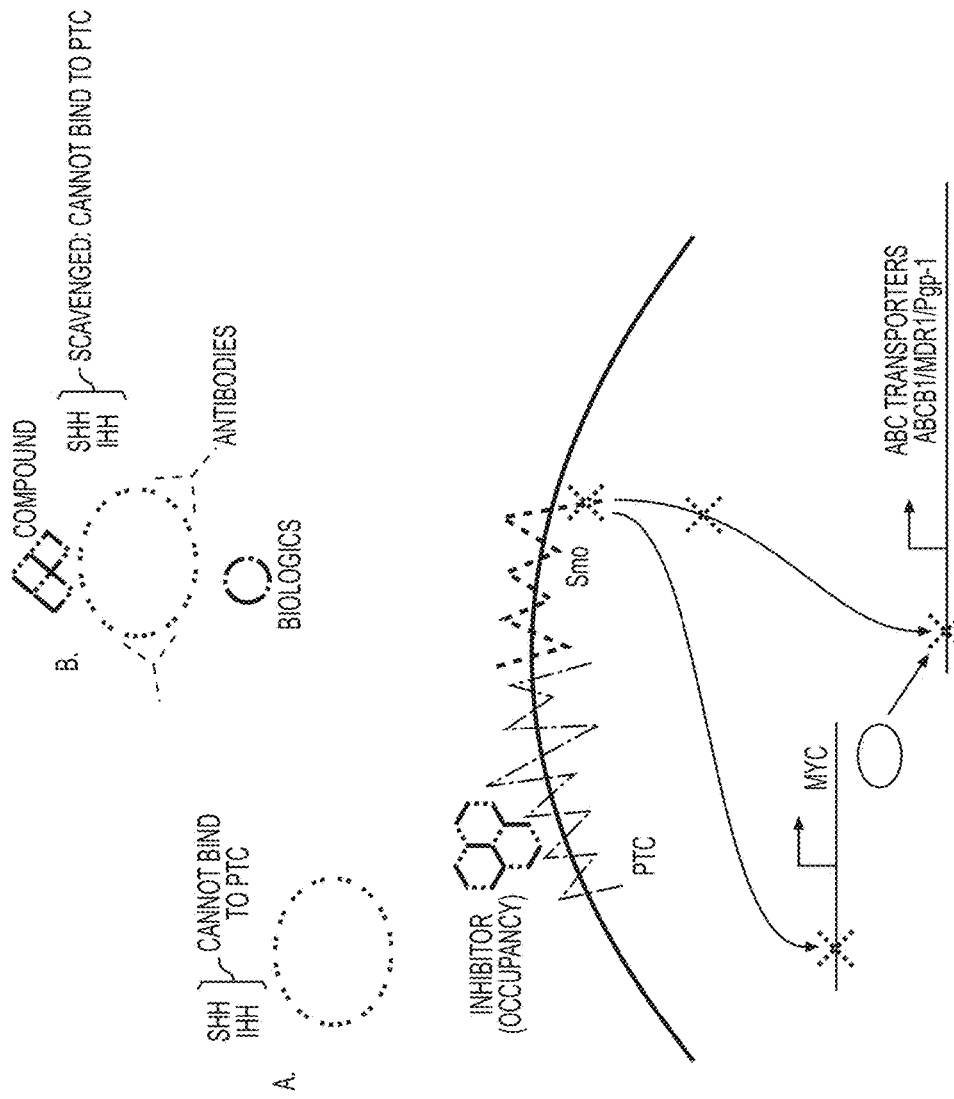
FIG. 2. A diagram illustrating an embodiment of the invention that uses competitive inhibitors or scavengers of the ligand Sonic and Indian hedgehog proteins to reduce MYC expression or other regulators and subsequently reduce downstream ABC transporter expression.

As shown in FIG. 2, the binding of Sonic or Indian hedgehog (SHH or IHH) to Ptc can be disrupted using competitive inhibitors (compounds or biologics) that occupy the binding site of SHH and IHH on Ptc (FIG. 2, left side). Also, the binding of SHH and IHH on Ptc can be prevented using therapies (compounds or biologics) that act as scavengers and bind SHH and IHH directly where they would normally bind Ptc (FIG. 2, right side). This would either prevent the activation of the pathway or inhibit an active pathway, which reduces MYC expression or activity of other regulators and subsequently ABC transporter expression.

Figure 3A:
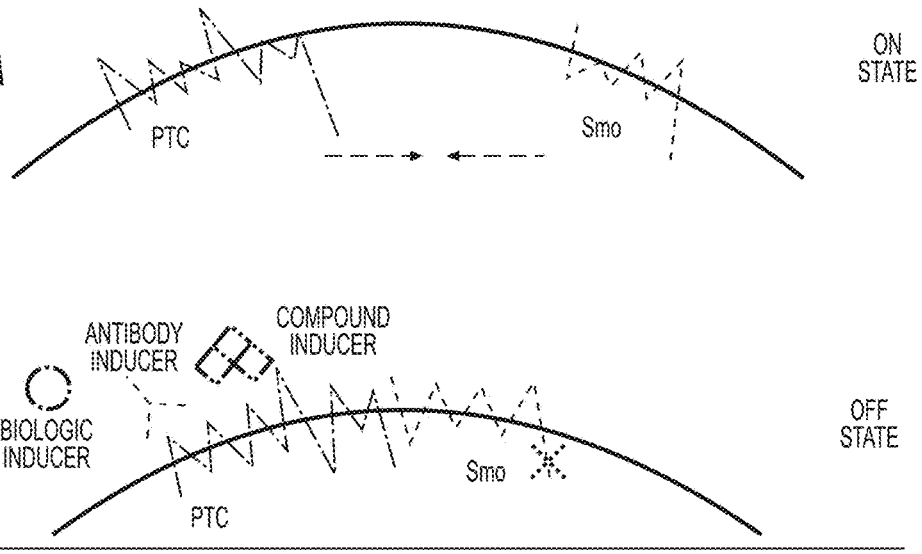
FIGS. 3A-3B. Diagrams illustrating embodiments of the invention involving the induction of patched or stabilization of the Ptc:Smo complex for the inhibition of smoothened receptor signaling to reduce MYC expression or other regulators and subsequently reduce downstream ABC transporter expression.
Figure 3B:
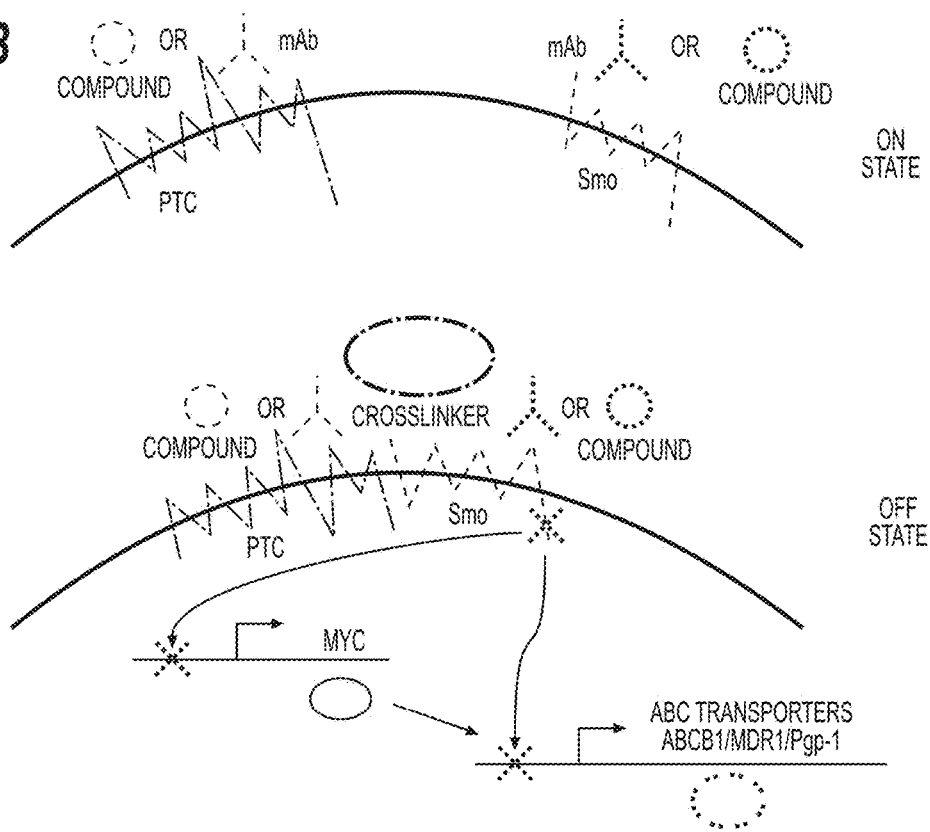

In another embodiment, compounds or biologics are used to induce Ptc activity to inhibit Smo activity or are used to stabilize the Ptc:Smo complex that results in the inhibition of the hedgehog pathway (FIGS. 3A-3B). The induction of Ptc activity is accomplished using compounds or biologics that cause molecular/conformational/structural changes to the receptor (FIG. 3A). The stabilization of the Ptc:Smo complex is accomplished using compounds or biologics that have the ability to crosslink the two receptors or by stabilization of the bound state of the two receptors (FIG. 3B). These compounds or biologics downregulate or prevent activation of the hedgehog pathway, which reduce MYC expression or activity of other regulators and subsequently ABC transporter expression.

Figure 4A:
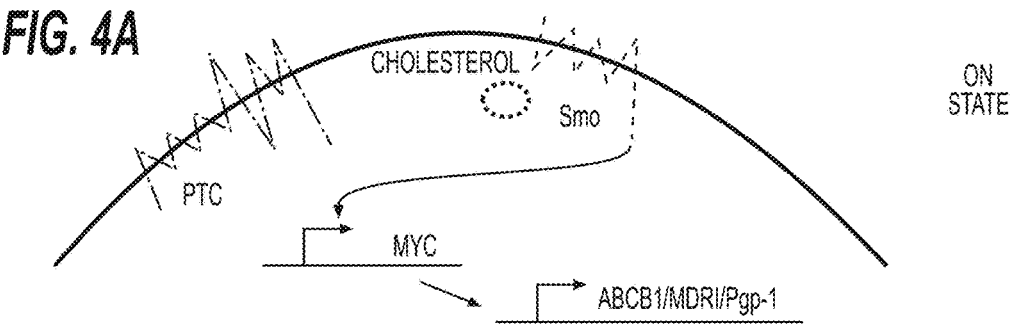
FIGS. 4A-4B. Diagrams illustrating embodiments of the invention using inhibitors of the cholesterol synthesis pathway or prevention of the sterolization or specifically cholesterolization of Smo.
Figure 4A:
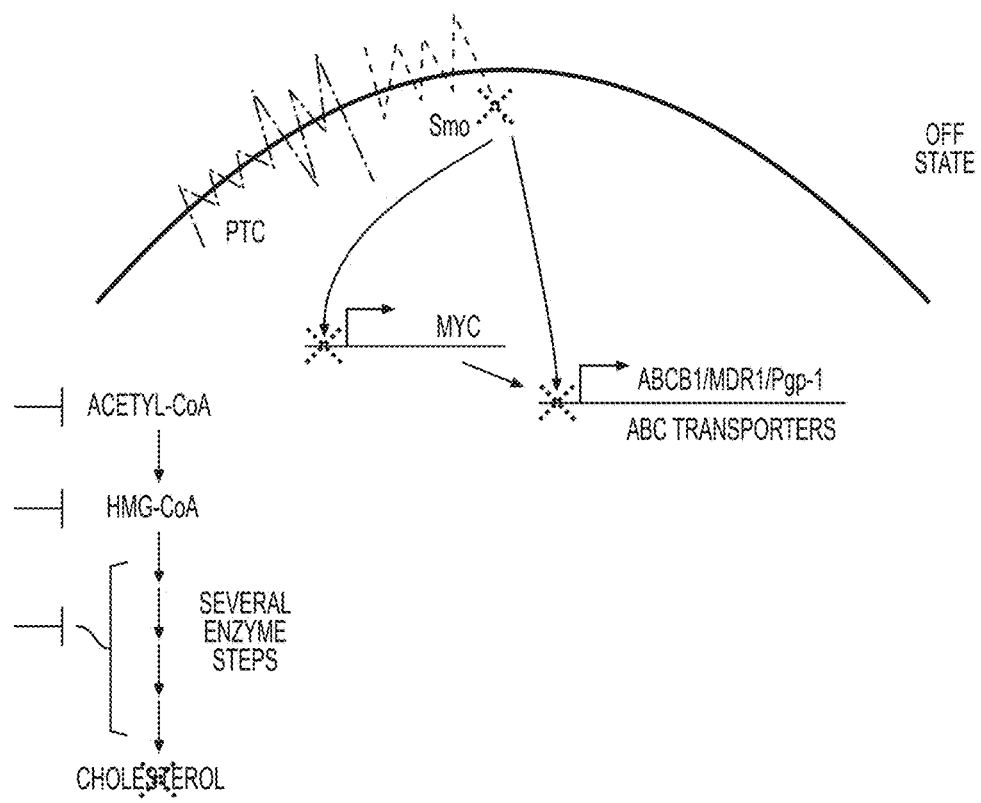
Figure 4B:
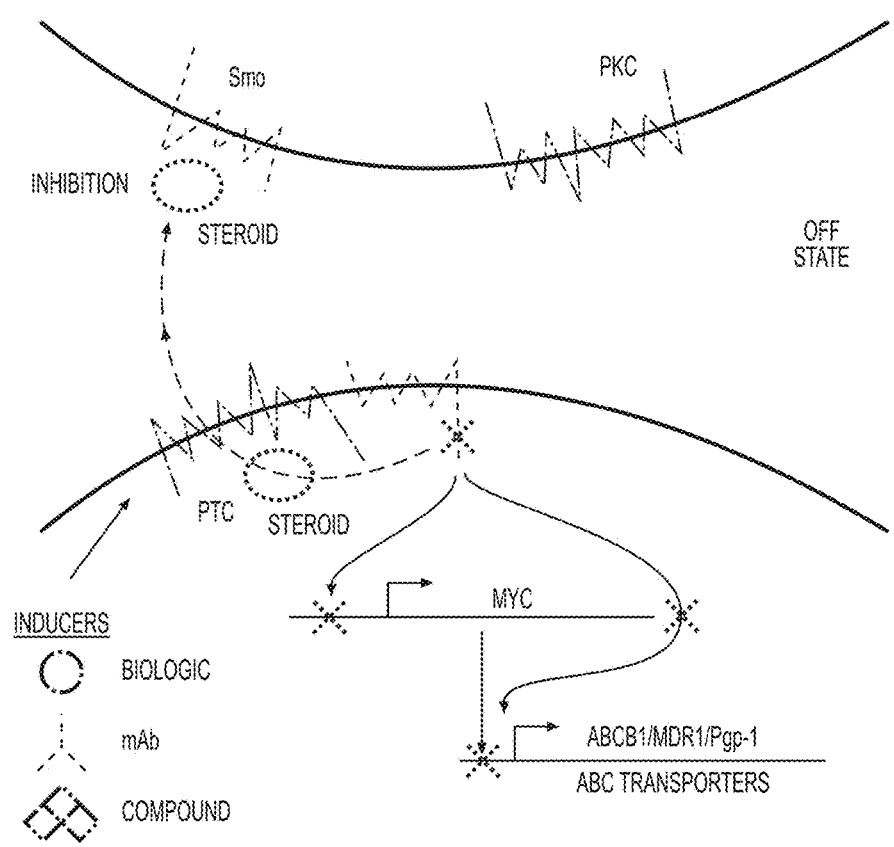

In another embodiment, compounds or biologics are used to prevent the cholesterol dependent activation of Smo by inhibition of enzymes in the cholesterol synthesis pathway. The inhibition of any enzymes that generate cholesterol precursors leads to the reduction of intracellular cholesterol that is necessary for Smo signaling activity (FIG. 4A). Also, the induction of Ptc pump activity can increase the removal the intracellular cholesterol that is necessary for Smo signaling activity (FIG. 4B). The reduction of cholesterol by either point of inhibition or induction either prevents the activation of the pathway or inhibits an active pathway, which reduces MYC expression or activity of other regulators and subsequently ABC transporter expression.

Figure 5:
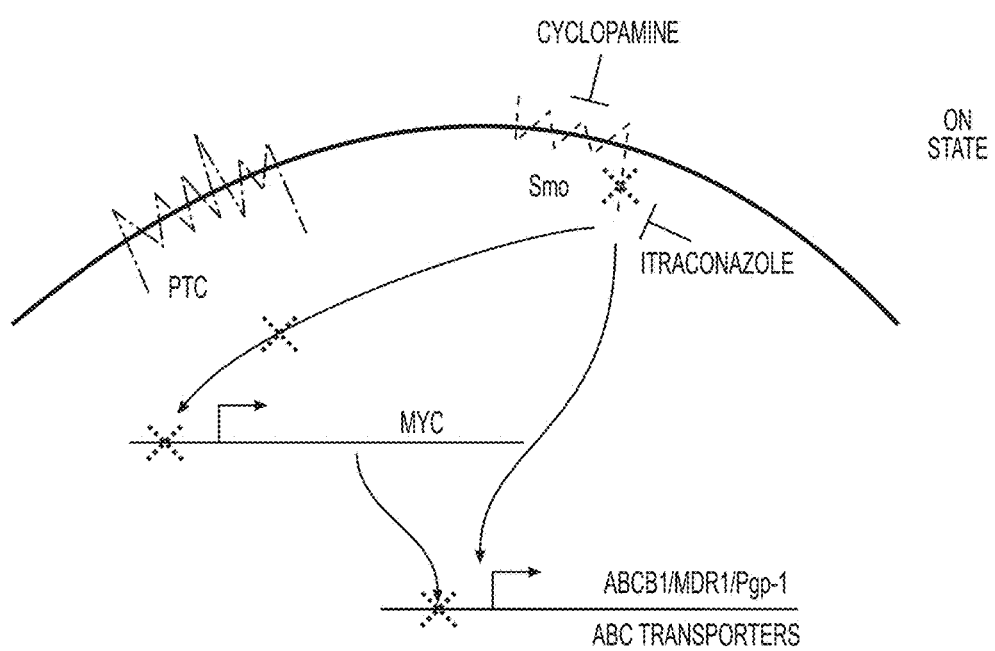
FIG. 5. A diagram illustrating an embodiment of the invention involving the direct inhibition of smoothened receptor signaling to reduce MYC expression or other regulators and subsequently reduce downstream ABC transporter expression.

In another embodiment, compounds or biologics are used to inhibit the activity of Smo. This is accomplished by using compounds or biologics that bind and antagonize Smo, which reduces MYC expression or activity of other regulators and subsequently downstream ABC transporter expression (FIG. 5).

Figure 6:
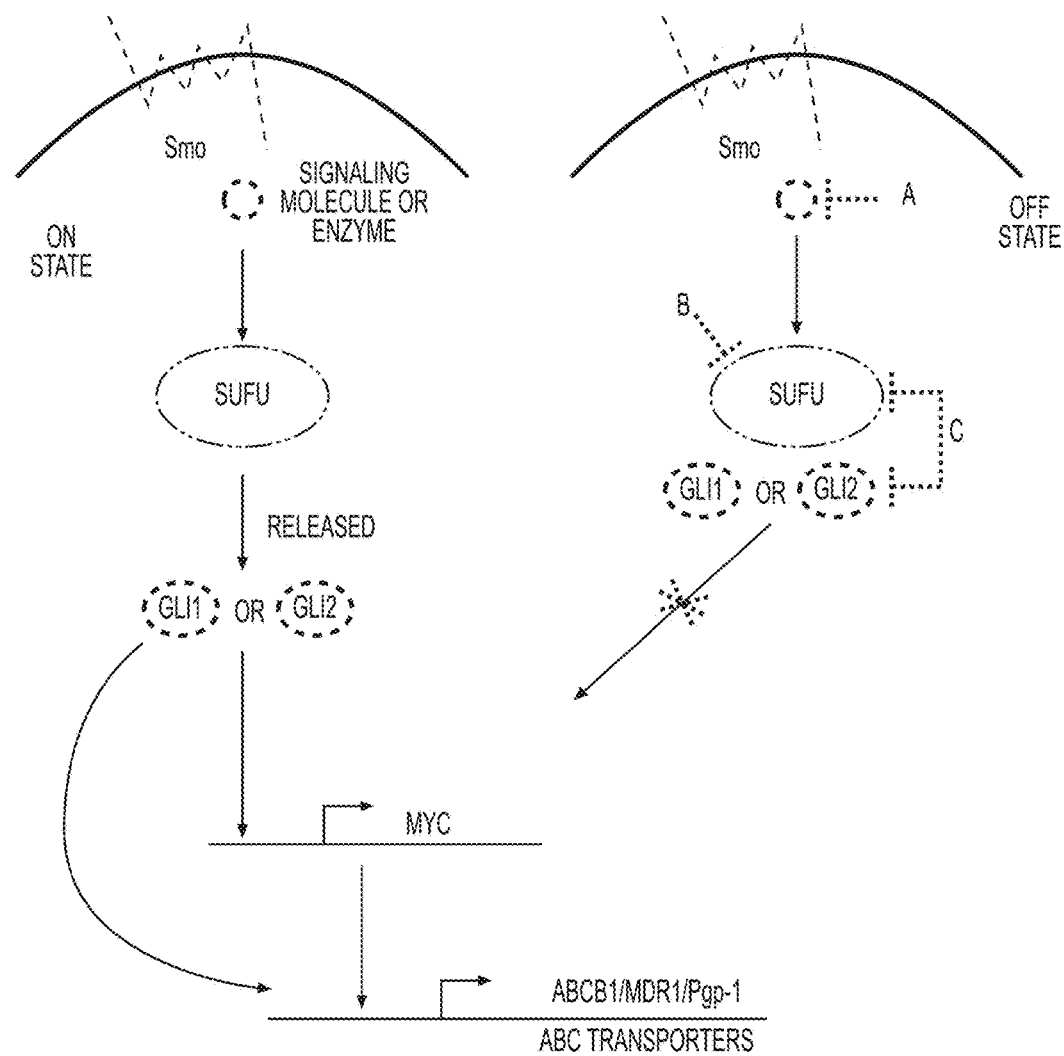
FIG. 6. A diagram illustrating an embodiment of the invention involving inhibition of effectors that relay signals to and activate SUFU for the reduction of MYC expression or other regulators and subsequently reduce downstream ABC transporter expression.

In another embodiment, compounds or biologics are used to inhibit signaling molecules that induce SUFU activity (e.g., at location "A" in FIG. 6, right side). The inactive state of SUFU sequesters downstream effector proteins such as Gli1 and Gli2, which stop downstream pathway activation.

In addition, compounds and biologics are used to inhibit SUFU activity (e.g., at location "B" in FIG. 6, right side) or stabilize SUFU:Gli complexes (e.g., at location "C" in FIG. 6, right side) directly and render the pathway inactive, which reduces MYC expression or activity of other regulators and subsequently downstream ABC transporter expression.

Figure 7:
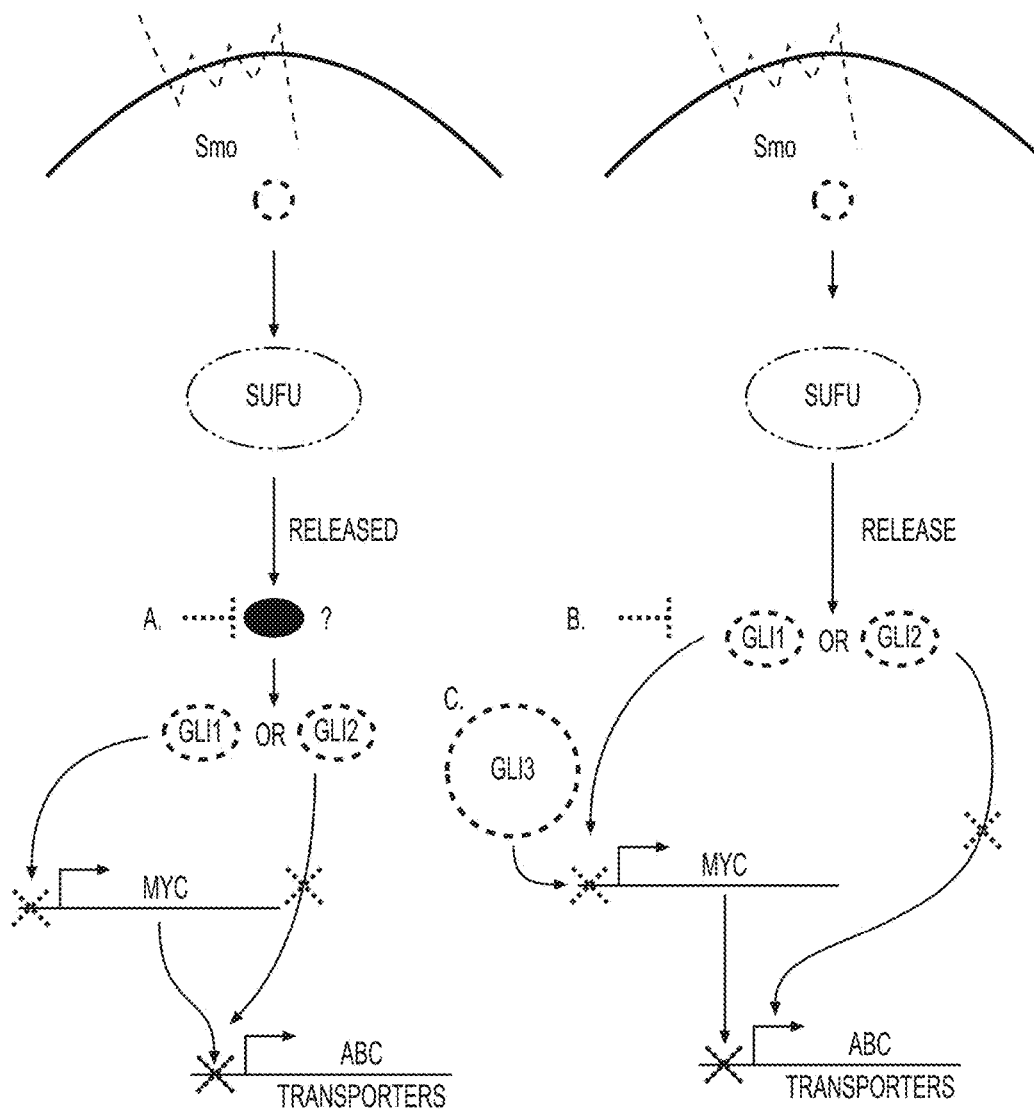
FIG. 7. A diagram illustrating an embodiment of the invention involving inhibition of Gli1, Gli2 and induction of Gli3 to reduce MYC expression or other regulators and subsequently reduce downstream ABC transporter expression.

In another embodiment, compounds or biologics are used to inhibit molecules that induce Gli1 or Gli2 transcription factor activity (e.g., at location "A" in FIG. 7, left side). In addition, compounds or biologics are used to inhibit Gli1 or Gli2 transcription factor activity directly (e.g., at location "B" in FIG. 7, right side) or to induce the activity of Gli3 (e.g., at location "C" in FIG. 7, right side), which reduces MYC expression or activity of other regulators and subsequently downstream ABC transporter expression.

Figure 8:
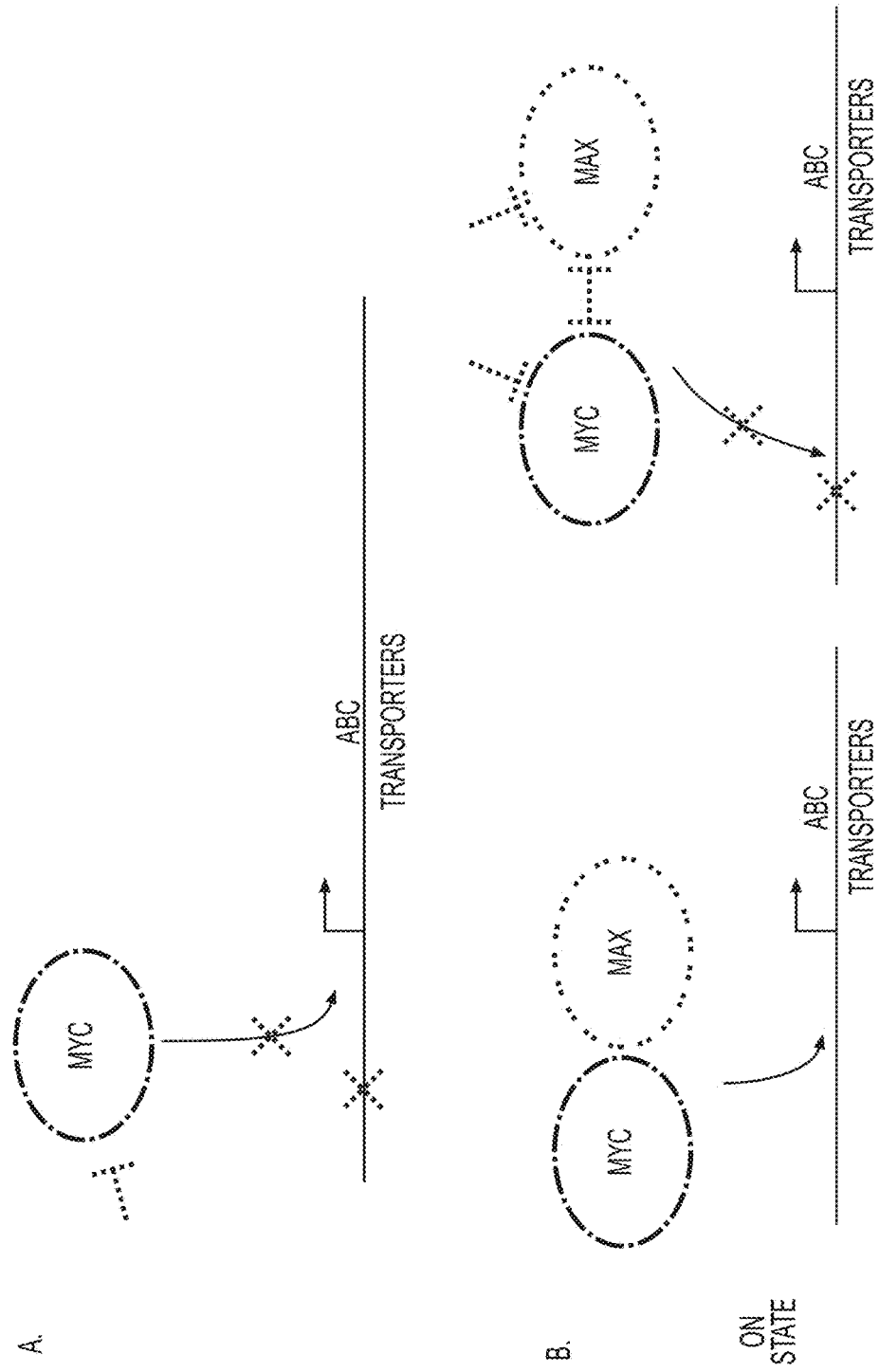
FIG. 8. A diagram illustrating an embodiment of the invention that uses the inhibition or reduction of MYC to directly or indirectly downregulate ABC transporter expression.

In another embodiment, compounds or biologics are used to inhibit the activity of MYC transcription factor for the reduction of ABC transporter expression. This is accomplished by using compounds or biologics to disrupt the binding of MYC to DNA binding sites through inhibition of MYC (e.g., FIG. 8, top), or by disruption of MYC:MAX complex formation (e.g., FIG. 8, bottom) that prevents the activation of target genes, specifically ABC transporters.

Figure 9:
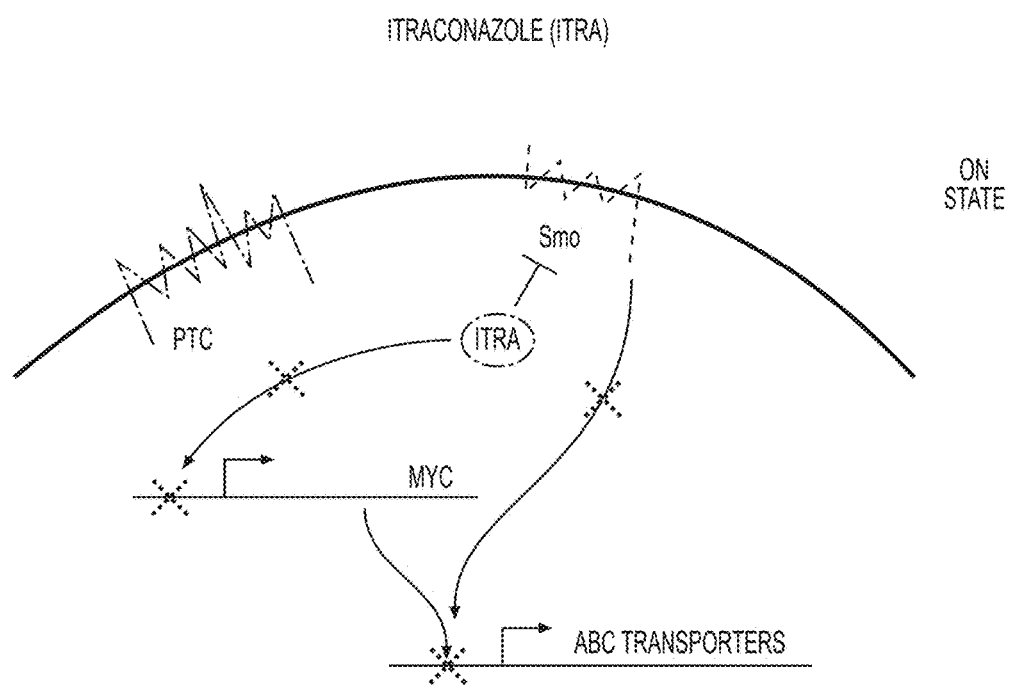
FIG. 9. A diagram illustrating a preferred embodiment of the invention demonstrating the use of itraconazole to inhibit Smo signaling thereby reducing MYC expression or other regulators and subsequently reduce downstream ABC transporter expression and thus sensitizing resistant cancer cells to chemotherapy drugs.
Figure 10I:
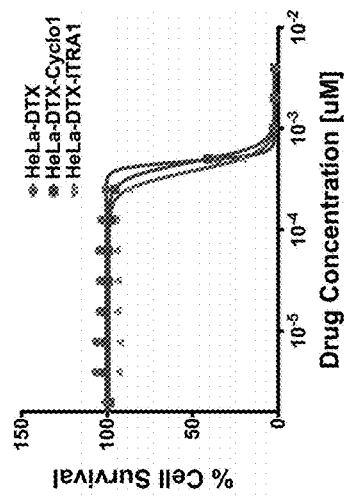
Figure 10J:
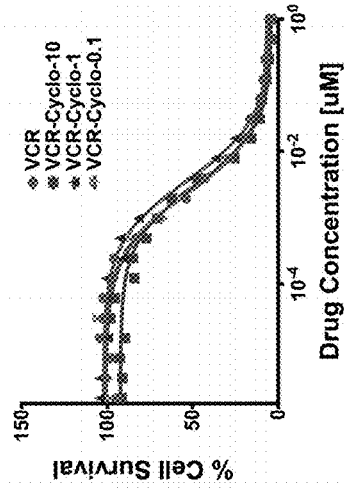
Figure 10K:
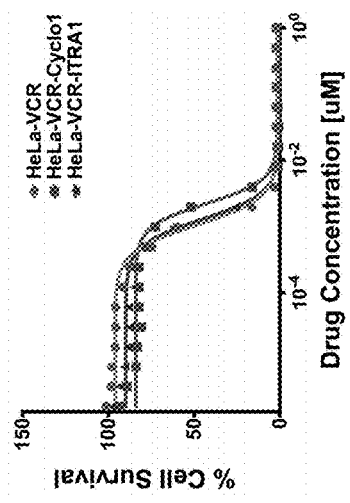
Figure 10L:
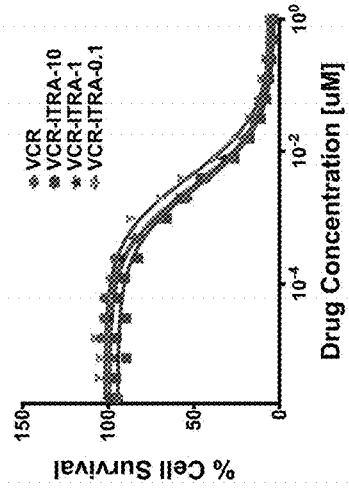

In preferred embodiments, synergistic killing of resistant cancer cells is achieved by combining the FDA approved drugs, for example itraconazole, arsenic trioxide, vitamin D3, or various other hedgehog pathway modulators (see Table 1), with a chemotherapeutic drug. Itraconazole and the other hedgehog pathway modulators can make resistant cancer cells vulnerable to chemotherapeutic drugs at lower concentrations while reducing the toxicity to the patient. FIG. 9 shows how the inhibition of Smo signaling by itraconazole reduces MYC expression or activity of other regulators and subsequent downstream ABC transporter expression and thus sensitizes resistant cancer cells to chemotherapy drugs.

Chemotherapeutic drugs for use in all aspects of the invention include, without limitation, vinca alkaloids, taxanes, platinums, anthracyclines, topoisomerase inhibitors, and kinase inhibitors. These drugs can be excreted from cells by ABC transporters, and the use of itraconazole, arsenic trioxide, vitamin D3, or other hedgehog pathway modulators, in combination with one or more of the chemotherapeutic drugs provides an improved therapeutic index for the drug or drugs.

The compositions, packaged pharmaceuticals, and methods of the instant disclosure, are advantageous in their use of an approved FDA antineoplastic agent, itraconazole, arsenic trioxide, vitamin D3, or another hedgehog pathway modulator, not as a single agent to treat tumors with tumorigenic mutations in the hedgehog pathway, but to inhibit hedgehog signaling to reduce MYC expression or activity of other regulators and subsequently ABC transporter expression that confers resistance in tumors. In addition, the dosages, toxicities, and ADME information have been well documented for itraconazole, arsenic trioxide, vitamin D3, and other hedgehog pathway modulators, and therefore can be more tolerable to the patient as compared to cyclopamine or new experimental drugs. The dosages needed in humans to down-regulate hedgehog regulated chemoresistance in cancer cells are readily determined during clinical trials, as is understood by those of ordinary skill in the art. In addition, the minimum effective dose (MED) and maximum tolerated dose (MTD) of itraconazole, arsenic trioxide, vitamin D3, and other hedgehog pathway modulators, provide parameters for more effective treatment of these tumors. These parameters thus allow physicians to prescribe and assess the efficacy with familiarity as compared to highly toxic hedgehog inhibitors like cyclopamine, and experimental drugs where dosages and toxicities are unknown. This effect may also be achievable by reducing the concentration of the hedgehog pathway modulators to reduce toxicity or side effects to patients in a first-line therapy setting, and not excluding a second-line therapy setting. The reduction in resistance mechanisms can increase the therapeutic index of chemotherapy drugs required to kill tumor cells, which then can reduce or circumvent toxicities known to affect patients during therapy.

Exemplary hedgehog pathway modulators usefully employed in the instant compositions, packaged pharmaceuticals, and methods include the agents listed in Table 1, without limitation.

TABLE 1

Hedgehog Pathway Modulators

Itraconazole
Arsenic trioxide
Vitamin D3
Saperconazole
Vismodegib (GDC-0449)
Erismodegib/Sonidegib (LDE225)
Taladegib
XL139 (BMS-833923)
Glasdegib (PF-04449913)
Saridegib (IPI-926)
Auranofin
GANT58
GANT61
Robotnikinin
MRT 10
M 25
U 18666A
RU-SKI 43
JK 184
HPI1
Eggmanone
Ciliobrevin A
AZ 12080282
AY 9944
SMANT
SANT-1
SANT-2
PF 5274857
Jervine
IHR1
TAK-441

In some embodiments, the hedgehog pathway modulator may be provided as a solid dispersion of the modulator in a polymer, for example to improve the absorption of drugs in the gastrointestinal tract and thus to achieve bioavailability compared to conventional formulations. Such dispersions may, for example, improve the dissolution of poorly soluble drugs compared to their normal crystalline forms. Itraconazole has been formulated in such dispersions in combination with HP-50 (see, SUBA Itraconazole from MayneP-harma, Raleigh, N.C. 27609, USA).

The disclosure thus provides in some aspects methods of treatment comprising:
administering to a mammalian subject a hedgehog pathway modulator; and
administering to the subject a chemotherapeutic agent; wherein the subject suffers from cancer, and wherein the hedgehog pathway modulator is administered in an amount effective to sensitize a tumor cell in the subject to the chemotherapeutic agent.

In some embodiments the chemotherapeutic agent is administered at a lower dose than would be required in the absence of the hedgehog pathway modulator. In some embodiments the hedgehog pathway modulator is administered below a maximum tolerated dose, and the chemotherapeutic agent is administered at a lower dose than would be required in the absence of the hedgehog pathway modulator. In some embodiments the hedgehog pathway modulator and the chemotherapeutic agent are administered simultaneously or nearly simultaneously.

In some embodiments the hedgehog pathway modulator is administered prior to administration of the chemotherapeutic agent. Variants of these methods comprise the single step of:
administering to a mammalian subject a chemotherapeutic agent; wherein the subject suffers from cancer, and wherein the subject has previously been administered a hedgehog pathway modulator in an amount effective to sensitize a tumor cell in the subject to the chemotherapeutic agent. In these methods, previous administration of the hedgehog pathway modulator may be done at any suitable time prior to administration of the chemotherapeutic agent, so long as a sufficient sensitization effect from the hedgehog pathway modulator administration remains in the subject, as would be understood by those of ordinary skill in the art.

According to other method embodiments, a hedgehog pathway modulator is administered after the administration of a chemotherapeutic agent.

In preferred method embodiments, the mammalian subject has not previously been treated with a chemotherapeutic agent prior to treatment with a hedgehog pathway modulator.

In some method embodiments the hedgehog pathway modulator and the chemotherapeutic agent are each independently administered orally, intramuscularly, or intravenously.

In specific embodiments, the hedgehog pathway modulator is itraconazole.

In another aspect, the disclosure provides novel compositions, packaged pharmaceuticals, and methods according to the following numbered paragraphs:
1. A composition comprising:
    a hedgehog pathway modulator; and
    a chemotherapeutic agent.
2. The composition of paragraph 1, wherein the hedgehog pathway modulator sensitizes a tumor cell to the chemotherapeutic agent.
3. The composition of paragraph 1, further comprising a pharmaceutically acceptable carrier.
4. A packaged pharmaceutical comprising the composition of any one of paragraphs 1-3 and instructions for using the composition to treat cancer in a mammalian subject.
5. A method of treatment comprising:
    administering to a mammalian subject a hedgehog pathway modulator; and
    administering to the subject a chemotherapeutic agent; wherein the subject suffers from cancer and wherein the hedgehog pathway modulator is administered in an amount effective to sensitize a tumor cell in the subject to the chemotherapeutic agent.
6. The method of paragraph 5, wherein the chemotherapeutic agent is administered at a lower dose than would be required in the absence of the hedgehog pathway modulator.
7. The method of paragraph 5, wherein the hedgehog pathway modulator and the chemotherapeutic agent are administered simultaneously.
8. The method of paragraph 5, wherein the hedgehog pathway modulator is administered prior to the administration of the chemotherapeutic agent.

9. A composition comprising:
   arsenic trioxide; and
   a chemotherapeutic agent.
10. The composition of paragraph 9, wherein the arsenic trioxide sensitizes a tumor cell to the chemotherapeutic agent.
11. The composition of paragraph 9, further comprising a pharmaceutically acceptable carrier.
12. A packaged pharmaceutical comprising the composition of any one of paragraphs 9-11 and instructions for using the composition to treat cancer in a mammalian subject.
13. A method of treatment comprising:
   administering to a mammalian subject arsenic trioxide; and
   administering to the subject a chemotherapeutic agent; wherein the subject suffers from cancer and wherein the arsenic trioxideis administered in an amount effective to sensitize a tumor cell in the subject to the chemotherapeutic agent.
14. The method of paragraph 13, wherein the chemotherapeutic agent is administered at a lower dose than would be required in the absence of the arsenic trioxide.
15. The method of paragraph 13, wherein the arsenic trioxide and the chemotherapeutic agent are administered simultaneously.
16. The method of paragraph 13, wherein the arsenic trioxide is administered prior to the administration of the chemotherapeutic agent.
17. A composition comprising:
   GDC-0449; and
   a chemotherapeutic agent.
18. The composition of paragraph 17, wherein the GDC-0449 sensitizes a tumor cell to the chemotherapeutic agent.
19. The composition of paragraph 17, further comprising a pharmaceutically acceptable carrier.
20. A packaged pharmaceutical comprising the composition of any one of paragraphs 17-19 and instructions for using the composition to treat cancer in a mammalian subject.
21. A method of treatment comprising:
   administering to a mammalian subject GDC-0449; and
   administering to the subject a chemotherapeutic agent; wherein the subject suffers from cancer and wherein the GDC-0449 is administered in an amount effective to sensitize a tumor cell in the subject to the chemotherapeutic agent.
22. The method of paragraph 21, wherein the chemotherapeutic agent is administered at a lower dose than would be required in the absence of the GDC-0449.
23. The method of paragraph 21, wherein the GDC-0449 and the chemotherapeutic agent are administered simultaneously.
24. The method of paragraph 21, wherein the GDC-0449 is administered prior to the administration of the chemotherapeutic agent.
25. A composition comprising:
   itraconazole; and
   a chemotherapeutic agent.
26. The composition of paragraph 25, wherein the itraconazole sensitizes a tumor cell to the chemotherapeutic agent.
27. The composition of paragraph 25, further comprising a pharmaceutically acceptable carrier.
28. A packaged pharmaceutical comprising the composition of any one of paragraphs 25-27 and instructions for using the composition to treat cancer in a mammalian subject.
29. A method of treatment comprising:
   administering to a mammalian subject itraconazole; and
   administering to the subject a chemotherapeutic agent; wherein the subject suffers from cancer and wherein the itraconazole is administered in an amount effective to sensitize a tumor cell in the subject to the chemotherapeutic agent.
30. The method of paragraph 29, wherein the chemotherapeutic agent is administered at a lower dose than would be required in the absence of the itraconazole.
31. The method of paragraph 29, wherein the itraconazole and the chemotherapeutic agent are administered simultaneously.
32. The method of paragraph 29, wherein the itraconazole is administered prior to the administration of the chemotherapeutic agent.
33. A composition comprising:
   vitamin D3; and
   a chemotherapeutic agent.
34. The composition of paragraph 33, wherein the vitamin D3 sensitizes a tumor cell to the chemotherapeutic agent.
35. The composition of paragraph 33, further comprising a pharmaceutically acceptable carrier.
36. A packaged pharmaceutical comprising the composition of any one of paragraphs 33-35 and instructions for using the composition to treat cancer in a mammalian subject.
37. A method of treatment comprising:
   administering to a mammalian subject vitamin D3; and
   administering to the subject a chemotherapeutic agent; wherein the subject suffers from cancer and wherein the vitamin D3 is administered in an amount effective to sensitize a tumor cell in the subject to the chemotherapeutic agent.
38. The method of paragraph 37, wherein the chemotherapeutic agent is administered at a lower dose than would be required in the absence of the vitamin D3.
39. The method of paragraph 37, wherein the vitamin D3 and the chemotherapeutic agent are administered simultaneously.
40. The method of paragraph 37, wherein the vitamin D3 is administered prior to the administration of the chemotherapeutic agent.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

The following examples demonstrate application of the inventive compositions and methods both in vitro and in vivo.

Example 1

Cancer cells grown in vitro are treated with chemotherapy drugs alone or simultaneously with a hedgehog pathway modulator, including itraconazole. The difference in cell death between cells treated with chemotherapy drugs alone or in simultaneous treatment with the hedgehog pathway modulators determines the degree of synergistic killing effect of the combination therapy. A two-dimensional dose response where a serial ten fold dose de-escalation of cyclopamine and itraconazole was performed to demonstrate sensitization to vincristine and docetaxel in naïve cell lines that have never been exposed to chemotherapy in the patients prior to isolation and establishment as a model of first-line of therapy: H295, Kelly, and resistant cell lines that have been exposed to chemotherapy prior to isolation and establishment: as a model of second-line of therapy: HeLa, and Caco-2 cells. As cyclopamine and itraconazole was reduced from 10 micromolar to 1 micromolar to 0.1 micromolar, the concentration of chemotherapy necessary to stop proliferation as well as kill half of the amount of cells (IC50) increases, but yet remains less than concentration of chemotherapy alone (FIGS. 10A-10H). The HeLa and Caco-2 cell lines did not respond (FIGS. 10I-10L). This clearly demonstrates a broad range of sensitization of cancers to chemotherapies by itraconazole and suggests that other hedgehog modulators may have similar effects. Furthermore, this indicates that using less sensitizer or hedgehog modulator, including itraconazole may minimize toxicity and side effects while improving efficacy of the chemotherapy in the first-line of therapy settings. The data presented here demonstrate that cancers pre-exposed to chemotherapy drugs acquire resistant alterations that may prevent the cancer cells to response to the proposed sensitization strategy with hedgehog pathway modulators, including itraconazole, and therefore may be more useful in a first-line of therapy setting, but also useful in a second-line of therapy setting where residual cancer cells may be responsive to hedgehog pathway modulation.

Materials and Methods (In Vitro):

Cell culture: The H295 cell line was grown in DMEM (Dulbecco's Modified Eagles Medium), supplemented with insulin, transferring, and selenium, 10% Fetal bovine serum, and gentamicin. The Kelly cell line was grown in DMEM, supplemented with 10% Fetal bovine serum, and gentamicin. Cell-based experiments were conducted in a 37 degree incubator supplemented with 5% carbon dioxide.

In vitro Pharmacology: H295 cells were plated in a 96-well dish at a density of 10000 cells per well and Kelly cells were plated at a density of 2000 cells per well. After 16 hours, cells were treated with 2-fold dilutions of vincristine (VCR) or docetaxel (DTX). For sensitization experiments, tomatidine, cyclopamine, or itraconazole, were added to all of the wells at a concentration of 10 micromolar, 1 micromolar, or 0.1 micromolar. The cells were incubated until the untreated well reached maximum confluency at which time the cells do not divide rapidly.

MTT Assay: Drug containing media from all of the dishes were discarded and MTT solution was added at a concentration of 5 micrograms per ml. The dishes were returned to the incubator for 4 hours. The excess MTT substrate was discarded and a solubilization solution of acid treated isopropanol and triton X-100 was added to the dishes and shaken for 10 minutes. The dishes were read in a plate reader equipped to read wavelength of 570 nanometers, and 690 nanometers as reference.

Data Analysis: Raw data was normalized to untreated wells to determine percentage cell death and plotted on a logarithmic scale using Graphpad Prism 6 software.

Example 2

Hedgehog pathway modulators, including itraconazole, are used as a pretreatment to turn off the hedgehog pathway and thus to downregulate ABC transporter expression. This in turn reduces the efflux of chemotherapy drugs. The difference in cell death between cells treated with chemotherapy drugs and pretreated with the hedgehog pathway modulators determines the degree of synergistic killing effect of the combination therapy.

Example 3

Drug de-escalation determines the synergistic killing effects of the combination therapy, where a normal, determined dose of a hedgehog pathway modulator, including itraconazole, is given, but the dose of the chemotherapy is reduced gradually in each study. De-escalation studies demonstrate whether or not the combinations reduce side effects of the hedgehog pathway modulator and known toxicities of the chemotherapy drugs to the patient while maintaining efficacious killing of the tumor.

Example 4

Figure 11:
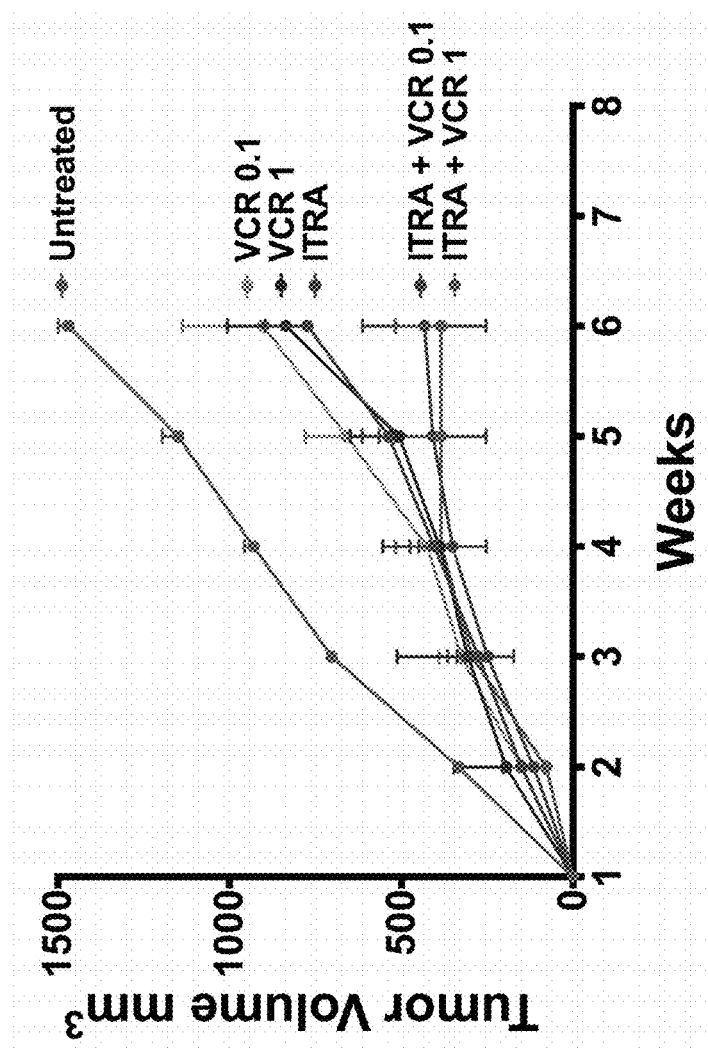
FIG. 11. A set of pre-clinical data demonstrating a preferred embodiment of the invention demonstrating a "dose de-escalation" strategy with H295 cell injected tumors in vivo treated with itraconazole, vincristine, itraconazole combined with vincristine and de-escalation experiment; itraconazole combined with ten times less vincristine, and ten times less vincristine.

The efficacy of the in vitro studies are tested in vivo using genetically engineered mouse models, xenograft models, or orthotopic xenograft models. A dose de-escalation of vincristine was performed to demonstrate sensitization with itraconazole in H295 cell derived tumors. Mice containing 0.5 cm tumors were divided into six cohorts, untreated, or a tolerated dose of itraconazole or vincristine alone, itraconazole combined with vincristine, ten-fold less vincristine, and ten-fold less vincristine combined with itraconazole. The growth of tumors in the itraconazole combined with vincristine and ten-fold less vincristine cohorts were halted and became necrotic beyond six weeks demonstrating that the tumors had also undergone cell death indicating that less chemotherapy can be used in the presence of itraconazole (FIG. 11). The data presented here demonstrate that sensitization of cancers to chemotherapies by hedgehog pathway modulators, including itraconazole, requires less chemotherapy, which will reduce toxicity and side effects, without decreasing efficacy of the chemotherapies. The approaches may be used in first-line therapy settings, as well as in second-line settings where tumor cells are found to be responsive.

Materials and Methods (In Vivo):

Cells: H295 cells were cultured as indicated above.

In vivo xenografts: 1 million H295 cells were combined with matrigel and injected into the subcutaneous part of the skin over the left flank in NOD-SCID mice. After six weeks when tumors were grown to 0.5 centimeters, the animals were randomized and treated with saline only (untreated control), vincristine, ten times less vincristine (dose de-escalation control), itraconazole, vincristine combined with itraconazole, and ten times less vincristine combined with itraconazole (dose de-escalation). Tumors were measured once a week and size was determined using the formula ($½W \times L$)/2. Tumor growth for each cohort was plotted using Graphpad Prism 6.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method of treating cancer consisting of:
   administering to a mammalian subject a hedgehog pathway modulator,
   wherein the hedgehog pathway modulator is Itraconazole, and
   administering to the mammalian subject a single chemotherapeutic agent,
   wherein the chemotherapeutic agent is Vincristine or Docetaxel;
   wherein the mammalian subject suffers from cancer,
   wherein Itraconazole is administered at a concentration of 0.1 micro molar to 10 micro molar,
   wherein the effect of Vincristine or Docetaxel on a cancer cell is ten-fold or greater than would be in the absence of Itraconazole.

2. The method of claim 1, wherein the chemotherapeutic agent is administered at a lower dose than would be required in the absence of the hedgehog pathway modulator.

3. The method of claim 1, wherein the hedgehog pathway modulator and the chemotherapeutic agent are administered simultaneously or nearly simultaneously.

4. The method of claim 1, wherein the hedgehog pathway modulator is administered prior to the administration of the chemotherapeutic agent.

5. The method of claim 1, wherein the hedgehog pathway modulator is administered after the administration of the chemotherapeutic agent.

6. The method of claim 1, wherein the hedgehog pathway modulator and the chemotherapeutic agent are each independently administered orally, intramuscularly, or intravenously.

7. The method of claim 1, wherein the subject suffers from an adrenal cortical carcinoma, a neuroblastoma, a cervical cancer, a colon cancer, or a colorectal cancer.

8. The method of claim 1, wherein the tumor cell expresses an ABC transporter protein and/or a MYC family gene.

* * * * *